US008425925B2

(12) United States Patent
Kellerby

(10) Patent No.: US 8,425,925 B2
(45) Date of Patent: Apr. 23, 2013

(54) PESTICIDAL TAG

(75) Inventor: Joe D. Kellerby, Cody, WY (US)

(73) Assignee: Y-Tex Corporation, Cody, WY (US)

( * ) Notice: Subject to any disclaimer, the term of this patent is extended or adjusted under 35 U.S.C. 154(b) by 1055 days.

(21) Appl. No.: 12/042,711

(22) Filed: Mar. 5, 2008

(65) Prior Publication Data

US 2009/0004236 A1    Jan. 1, 2009

Related U.S. Application Data

(63) Continuation of application No. PCT/US2007/021243, filed on Oct. 3, 2007.

(60) Provisional application No. 60/947,265, filed on Jun. 29, 2007.

(51) Int. Cl.
*A01N 25/10* (2006.01)
*A01N 43/08* (2006.01)
*A01N 43/16* (2006.01)

(52) U.S. Cl.
USPC ........... 424/411; 424/403; 424/405; 424/406; 424/407; 424/409; 424/486; 424/487; 514/30

(58) Field of Classification Search ............ 424/411
See application file for complete search history.

(56) References Cited

U.S. PATENT DOCUMENTS

| | | | |
|---|---|---|---|
| 4,199,569 A | 4/1980 | Chabala et al. | |
| 4,310,519 A | 1/1982 | Albers-Schonberg et al. | |
| 4,847,243 A | 7/1989 | Wallace | |
| 5,262,400 A * | 11/1993 | Chu et al. ................ | 514/30 |
| 6,103,758 A * | 8/2000 | Sembo ................ | 514/471 |
| 7,910,122 B2 * | 3/2011 | Sirinyan et al. ........... | 424/411 |
| 2006/0288955 A1 | 12/2006 | Albright et al. | |

FOREIGN PATENT DOCUMENTS

| WO | WO 97/41742 | * 11/1997 |
|---|---|---|
| WO | 2004/002537 | 1/2004 |
| WO | WO 2006/000335 | * 1/2006 |

OTHER PUBLICATIONS

Wu et al in Zhiwu Baohu Xuebao (2003) 30,(4) 418-422 HCAPLUS abstract # 2004:395463 Doc. $ 141:345041 Effects of Synergists on Insecticide Susceptibility-.*
Dalzell, Bonnie, "Avermectins", http://www.clark.net/pub/bdalzell/21c/avermec.html, printed Jul. 14, 1999, pp. 1-2.

(Continued)

*Primary Examiner* — Neil Levy
(74) *Attorney, Agent, or Firm* — Harness, Dickey & Pierce, P.L.C.

(57) ABSTRACT

Pesticidal compositions and articles providing topical application of a mixture of (1) a macrolide of the avermectin/milbemycin class, such as, but not limited to ivermectin, abamectin, or milbemectin, and (2) a synergist of the aryl aliphatic ether-class, such as, but not limited to piperonyl butoxide, present in (3) a weight ratio of synergist:macrolide that is great than 1:1. The compositions and articles demonstrate efficacy, even in point-of-contact applications, against various pests of domestic animals, such as, but not limited to arthropod ectoparasites including horn flies and buffalo flies. Methods are provided in which compositions can be employed as pour-ons, spot-ons, dusts, or sprays for direct topical application to the domestic animal; or in which articles comprising a polymer resin base, such as an ear tag, from which the active ingredients of the composition can be released, are affixed to the animal to provide long-term delivery.

22 Claims, 1 Drawing Sheet

OTHER PUBLICATIONS

Hoelscher et al., http://entowww.tamu.edu/extension/bulletins/b-1306.html, "Suggestions for Managing External Parasites of Texas Livestock and Poultry", Texas Agricultural Extension Service, Oct. 15, 1997 (printed Jul. 14, 1999), pp. 1-39.

http://128.227.103.58/tmp/blood.html, "Bloodsucking Insects", University of Florida, Institute of Food and Agricultural Sciences, printed Aug. 6, 1998, pp. 1-2.

http://aphisweb.aphis.usda.gov/oa/screwworm.html, "Eradicating Screwworms from North America", APHIS Web—Screwworm Eradication, USDA Animal and Plant Health Inspection Service, printed Aug. 6, 1998, pp. 1-4.

http://eru.usask.ca/livestok/wclp/dairy2/d2horfly.htm, "Recommendations for the Control of Arthropod Pests of Livestock and Poultry in Western Canada; Dairy Cattle (Lactating)—Horn fly", the Western Committee on Livestock Pests (WCLP), printed Mar. 4, 1999, pp. 1-6.

http://eru.usask.ca/livestokk/wclp/pests/Horn.htm, Horn fly, *Haematobia irritans* (L.), WCLP Pests/WCLP Hosts, printed Mar. 4, 1999, pp. 1-8.

http://fadr.msu.ru/rodale/agsieve/txt/vol3/6/a2.html, "Invermectin Controls Parasites", Foundation for Agrarian Development Research (fadr), Jan. 15, 1996 (printed Mar. 4, 1999), pp. 1-2.

http://leaky.rock.tap.csiro.au/facts/bfflyvac__txt.html, "Buffalo Fly Vaccine, Irritating flies affect cattle growth", Tropical Beef Centre, printed Aug. 6, 1998, pp. 1-2.

http://pmep.cce.cornell.edu/profiles/insect-mite/abmectin-buffencarb/avermectin/abamec-ext.html, "avermectin (Agri-Mek, Affirm) p. 1", Mar. 17, 1998 (printed Mar. 4, 1999), pp. 1-7.

http://res.agr.ca/ecorc/program2/entomology/biting__flies/english/hornfly.html, "Life cycle of the horn fly", printed Mar. 4, 1999, p. 1 of 1.

http://taxonomy.zoology.gla.ac.uk/ToL/Phthiraptera/links/phoresy.html, "Phoresy, Phoretic relationships between lice and Hippoboscid flies", Colins Publishers, 1952, pg. 1.

http://ucdnema.ucdavis.edu/imagemap/nemmap/ent156html/204NEM/BSTREPTO, "*Streptomyces avermitilus*", printed Mar. 4, 1999, p. 1.

http://www.abvt.org/iverm.html, "The American Board of Vetrenarian (ABVT), Ivermectin Toxicosis", printed Jul. 20, 1999, pp. 1-5.

http://www.afg.gov.bc.ca/croplive/cropprot/livestck.htm, "Control of Insect and Related Pests of Livestock and Poultry in British Columbia, Pest Management Factsheet 98-02, revised May 1998", British Columbia Government, May 1998 (printed Mar. 4, 99), pp. 1-8.

http://www.biok.com.cn/p2e.htm, "Ivermectin B1" (chemical formula), printed Jul. 14, 1999, pp. 1-2.

http://www.biok.com.cn/ple.htm, Avermectin B1 (chemical formula), printed Jul. 14, 1999, p. 1.

http://www.ccp.com/~angus/journal/98__05may/vetcall.htm, "Control of horn flies and face flies on beef cattle", The Angus Journal—Vet Call, The Angus Journal, May 1998 (printed Mar. 4, 1999), pp. 1-4.

http://www.missouri.edu/~vmicrorc/Arthropods/Diptera/Haematob.htm, "Horn Fly", printed Aug. 6, 1998, pp. 1-2.

http://www.novartis.ca/product/hornfly.htm, "Horn Fly Control Increases Profitability", Novartis AHC Inc.—Product Information, 1997, pp. 1-3 (printed Mar. 4, 1999).

http://www.oznet.ksu.edu/Entomology/extension/InsectID/Mock/hornfly.htm, "Horn fly, *Haematobia irritans*", KState Research & Extension, printed Mar. 4, 1999, pp. 1-2.

http://www.y-tex.com.GardStar.html, "GardStar® plus Insecticide Cattle Ear Tag, GardStar Product Advantages", Y-Tex, printed Jul. 20, 99, pp. 1-2.

http://www.y-tex.com/fly-tag.html, Insecticide Ear Tags, printed Jul. 20, 1999, pp. 1-3.

http://www.y-tex.com/Max-Con.html, Max-Con™ Insecticide Cattle Ear Tag, Max-Con Product Advantages, Y-Tex, printed Jul. 20, 1999, pp. 1-2.

http://www.y-tex.com/OPtimizer.html, OPtimizer™, Insecticide Cattle Ear Tag, OPtimizer Product Advantages, Y-Tex, printed Jul. 20, 1999, pp. 1-2.

Powell, Peggy K., PhD., http://www.caf.wvu.edu/~forage/10623.htm, "Horn Fly Biology and Management", West Virginia University Extension Service, Feb. 1995, pp. 1-4 (printed Mar. 4, 1999).

G. Wu et al., "Effects of Synergists on Toxicity of Six Insecticides in Parasitoid Diaeretiella rapae (Hymenoptera: Aphidiidae)", Entomological Society of America, vol. 97, No. 6, 2004, pp. 2057-2066.

G. Wu et al., "Insecticide toxicity and synergism by enzyme inhibitors in 18 species of pest insect and natural enemies in crucifer vegetable crops", Society of Chemical Industry, Pest Management Science 63, 2007, pp. 500-510.

\* cited by examiner

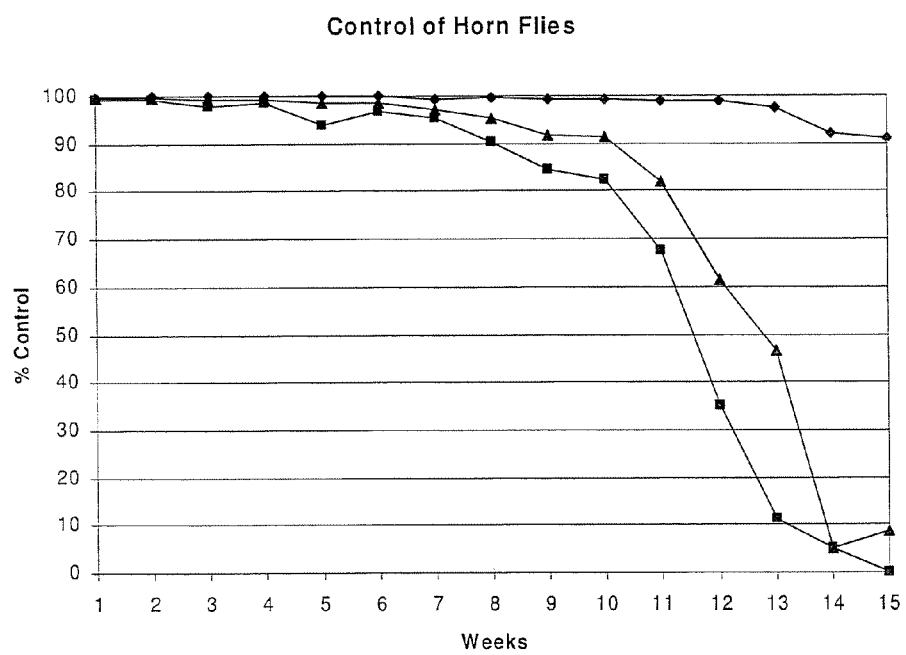

PESTICIDAL TAG

CROSS-REFERENCE TO OTHER APPLICATIONS

This application is a continuation of International Application No. PCT/US2007/021243, filed Oct. 3, 2007 and designating the United States, which claims the benefit of U.S. Provisional Application No. 60/947,265, filed Jun. 29, 2007. The disclosures of the above applications are incorporated herein by reference.

FIELD

The present disclosure relates generally to pesticidal active ingredient compositions and, more particularly, to compositions, methods and devices containing or employing a mixture of at least one avermectin/milbemycin-class compound, such as, but not limited to abamectin, ivermectin, or milbemectin, with a synergist, such as piperonyl butoxide, which together provide an improved anti-pest effect as a toxicant against parasites of the group Ecdysozoa. The present invention can be particularly useful as an active ingredient composition for preventing or treating pest-infestation of animals, that can be applied either topically or in a sustained release delivery system, such as a resin base, for pest infestation control.

BACKGROUND

The statements in this section merely provide background information related to the present disclosure and may not constitute prior art. Arthropods and their relatives are the most numerous of living organisms and nearly one million described species constitute approximately 70% of all animal species. Of these, about 1% are considered significant pests. These pests attack humans and/or their domestic animals; transmit human, animal, and plant diseases; destroy structures; and compete for available supplies of food and other natural resources. In the United States, there are at least 600 species of such economically significant pests.

In an effort to control the damage done by various pests, there has been widespread use and development of pesticides. Pesticides are generally defined as any substance or chemical designed or formulated to kill or control weeds or animal pests. Pesticides directed against animal pests include, e.g., insecticides, acaricides, helminthicides, molluscicides, and rodenticides, which are designed or formulated to either kill or control, respectively: insects, mites or ticks, worms, mollusks, and rodents. Generally, control is achieved by oral ingestion of stomach poisons, contact with poisons that penetrate through the cuticle, or inspiration of fumigants that penetrate through the respiratory system of the pest. Ancillary chemicals can also be employed in pest control and include attractants and repellants, which influence pest behavior, and chemosterilants, which influence reproduction. The control can practiced to prevent pest infestation or to treat an existing infestation, and the infestation can be of a type that is typically either long-term (e.g., as with lice) or transitory (e.g., as with biting flies).

The widespread use of chemical pesticides has resulted in increasing difficulties in practical pest control. Examples of such difficulties include: genetic selection under chemical pressure of strains of more than 400 arthropod (insect and acarine) pests that are resistant to one or more classes of pesticides and some to every available material; resurgences of pests and outbreaks of secondary pests that result from elimination of natural enemies by the use of broad-spectrum pesticides; adverse human-health effects from injudicious use of highly toxic pesticides; and exponentially increasing costs of developing new pesticides.

One area of particular concern is the protection of domestic animals, such as cattle and other livestock, from parasites. Parasites can be continuous or non-continuous, depending on whether the complete life cycle, or only particular stage(s) of the life cycle, is host-based; and non-continuous parasites can exhibit continually parasitic behavior during a particular life stage.

With respect to the protection of livestock and other domestic animals, significant advances have been made against previously pesticide-resistant species of livestock ectoparasites. For example, horn flies (*Haematobia irritans irritans*), a non-continuous ectoparasite, have been effectively controlled by the use of ear tags containing either pyrethroid or organophosphorus insecticides, including mixtures of organophosphates such as diazinon (i.e., a pyrimidine organothiophosphate) and chlorpyrifos (i.e., a pyridine organothiophosphate), impregnated in a resin base, from which it can be released. The impregnation can be achieved by contacting the resin base article with an active ingredient composition according to the present invention, but in various preferred embodiments, the active ingredient composition can be present in admixture with the resin base components prior to forming an article therefrom The insecticide mixture is slowly released from the resin base onto the skin (epidermis and/or hair) of the animal and exhibits good contact toxicity results with respect to various pests, including horn flies, stable flies, and ticks. A complete discussion of this technology can be found in commonly-assigned U.S. Pat. No. 5,472,955, the entire disclosure being incorporated herein by reference. An ear tag containing a mixture of diazinon and chlorpyrifos is readily commercially available from Y-Tex Corporation (Cody, Wyo.) and is being marketed under the trademark WARRIOR™.

Recently, another ear tag has been developed by Y-Tex Corporation and is being marketed under the trademark PYTHON®. This ear tag is similar to the WARRIOR™ ear tag in that a synergized insecticide is impregnated into a resin base. However, the PYTHON® ear tag differs primarily from the WARRIOR™ ear tag in that the impregnated insecticide is an enriched S-isomer, synthetic pyrethroid compound, as opposed to an organothiophosphate compound. A synthetic pyrethroid compound is generally defined as a synthetic pesticide that mimics pyrethrin, the original botanical pesticide derived from certain species of chrysanthemum flowers. Examples of pyrethroid compounds include, without limitation, allethrins, resmethrins, permethrins, and fenvalerates. The synthetic pyrethroids have the marked advantages of low to moderate toxicity to humans and domestic animals and high effectiveness at low application rates, often one-tenth of those required for organophosphorus and carbamate insecticides. The PYTHON® ear tag utilizes zeta-cypermethrin (empirical formula: $C_{22}H_{19}Cl_2NO_3$) as the insecticide. Zeta-cypermethrin (readily commercially available from FMC Corporation, Philadelphia, Pa.) is a mixture of stereoisomers comprising high concentrations of s-isomers of cypermethrin. The zeta-cypermethrin is then combined with a synergist, such as piperonyl butoxide (empirical formula: $C_{19}H_{30}O_5$), to produce a synergized insecticide. The PYTHON® ear tag exhibits excellent contact toxicity against horn flies (including horn flies with moderate pyrethroid resistance), face flies (*Musca autumnalis*), lice (Phthiraraptera order), Gulf Coast ticks (*Ambylomma maculatum*), and spinose ear ticks (*Otobius megnini*).

Other ear tags effective against certain ectoparasites are also readily commercially available from Y-Tex Corporation and are marketed under the trademarks OPTIMIZER® (containing diazinon and being generally effective against pyrethroid-resistant horn flies, face flies, Gulf Coast ticks, spinose ear ticks, and lice) and GARDSTAR® (containing permethrin and being generally effective against pyrethroid-susceptible horn flies, face flies, Gulf Coast ticks, spinose ear ticks, stable flies, house flies, and lice).

Although the aforementioned insecticidal compositions have aided greatly in the control and treatment of various livestock pests, some ectoparasites, especially horn flies and buffalo flies (*Haematobia irritans exigua*), are now developing resistance to these organophosphorus- and/or pyrethroid-based insecticidal compositions.

As a result, there is a need to provide new or improved pesticidal compositions of other chemical classes in order to allow alternation (i.e. rotation) of different types of pesticides so as to lessen the resistance, or decrease the rate of development of resistance, of local pest populations to any one of the pesticides included in a rotation program, and thereby provide effective whole-life treatment programs for livestock and other animals. A need for alternative pesticide compositions also arises because of variations in local pest species populations, as by, e.g., introduction of foreign pests, changes due to differing seasons or weather conditions, or by moves to different environments, such as indoor-outdoor habitats, wetland-woodland-field habitats, and geographic region habitats. Each of these factors can result in a given pesticide composition's become less effective as a protectant of the livestock or other treated animal, such that rotation with another pesticide composition would be beneficial.

Thus, recent attention has focused toward pesticide compounds that exhibit effectiveness against ectoparasites that have (or are) developing resistance to these organophosphorus- and/or pyrethroid-based insecticidal compositions. Among the compounds being actively developed are the pesticidal macrolides, which are a class of macrocyclic lactones of the polypropionate-type polyketides. Of particular interest among these compounds are those classified as 16-member macrolides, i.e. having a 16-member macrocyclic lactone ring core. Among these are compounds of the avermectin-milbemycin group, examples of which include the abamectins, ivermectins, and milbemectins.

The currently available active ingredient compositions containing one or more types of such macrolides, e.g., ivermectin, are delivered by whole-animal drenching with a pour-on solution, by injection, or by oral administration in relatively large doses. This is a difficult, time-consuming, and expensive undertaking for even a moderately sized livestock operation. Additionally, orally-administered active compositions are sometimes very difficult to administer to an uncooperative animal, especially cattle, and may not be well tolerated by the animal's digestive system. Further, the orally-administered composition may interfere with the animal's performance (e.g., weight gain or milk production) or may inadvertently poison the animal (e.g., avermectin toxicosis). Also, the pest still has to bite the animal in order to receive a toxic dose of an injected or orally administered formulation. Finally, the enteral, parenteral, and topical drenching routes of administration induce a much higher concentration of pesticide in the animal tissues, resulting in the need to comply with a mandatory livestock animal withdrawal period before slaughter, in order to permit metabolic degradation and secretion of the pesticide. Thus, it would be advantageous for all these reasons to provide a pesticidal macrolide formulation that is pesticidally effective, and that can be administered in a less invasive or less pervasive manner, such as with an ear tag. Yet, pesticidal macrolides have been found to exhibit too low a level of pesticidal contact activity to permit ear tag and other point-of-contact applications to be feasible.

Therefore, there exists a need for a safe, effective, ready-to-use, pesticidal macrolide active ingredient composition and method of use thereof for the long-term prevention and treatment of pest/parasite infestation in domestic animals, especially cattle and other livestock, wherein the pesticide composition can be easily incorporated into topical preparations and ear tags and which is effective against horn flies, buffalo flies and other ectoparasites, especially those that have developed (or are developing) resistance to organophosphate- and/or pyrethroid-based insecticidal compositions.

SUMMARY

In accordance with one embodiment of the present invention, an ear tag comprising an active ingredient composition is designed for attachment to the ear of a domestic animal for the prevention and treatment of pest infestation, as by pests of the group Ecdysozoa. The pest infestation can be by pests of the phylum Arthropoda. Ectoparasitic infestation can thereby be treated, such as infestation by an arthropod ectoparasite. The active ingredient composition includes at least one avermectin or milbemycin compound, such as, but not limited to abamectin, ivermectin or milbemycin. A synergist, preferably an aryl aliphatic ether such as, but not limited to piperonyl butoxide, is combined with the ivermectin or abamectin to produce a synergized active ingredient mixture. The synergized active ingredient mixture is then impregnated into a resin base, such as, but not limited to polyvinyl chloride, acrylonitrile-butadiene copolymer, polyurethane, and chlorinated polyethylene, and then formed into the shape of an ear tag. The ear tag is then fastened to the ear of the animal in such a manner so as to allow the tag to physically contact various parts of the animal's body. The synergized active ingredient mixture is released from the tag over the course of several months and is particularly effective against various ectoparasites of domestic animals, such as, but not limited to horn flies and buffalo flies.

Compositions according to the present invention have surprisingly been found capable of increasing the contact activity of these macrolide compounds, and can thus make it feasible to utilize avermectin/milbemycin-class macrolides, such as abamectin and ivermectin, in formulations for long-lasting control of insect and other pests. These compositions thereby permit the use of such macrolides to be extended to the point-of-contact pesticide field (e.g., impregnated ear tags, impregnated "hang-tags" attached to another unit such as an identification tag or halter, and spotting compositions such as spotting solutions), in which they had not been otherwise found effective. In some embodiments, by increasing the contact activity of the macrolide, a topical composition according to the present invention (e.g., a soak, rub, dip, spray, dust, or the like) can utilize a lesser concentration of biocidal macrolide than would otherwise be the case.

In accordance with another embodiment of the present invention, a topically applied active ingredient composition is provided for the prevention and treatment of pest infestation. The active ingredient composition includes at least one avermectin compound, such as, but not limited to ivermectin or abamectin. A synergist, such as, but not limited to piperonyl butoxide technical is combined with the ivermectin or abamectin to produce a synergized active ingredient formulation. The synergized active ingredient formulation is then topically applied to various parts of the animal's body for example, as a pour-on, spot-on, dust, and the like.

The synergized active ingredient formulation is effective over the course of several weeks and is particularly effective against various ecdysozoan parasites of domestic animals, such as, but not limited to horn flies and buffalo flies.

The present invention further provides:

Ear tags capable of controlling pests of domestic animals, the tags including a pesticidally effective amount of an active ingredient composition, impregnated in a polymer resin base from which it can be released, which composition contains (a) a macrolide component comprising an avermectin; and (b) a synergist component comprising a 1,3-benzodioxole synergist compound; with (c) the weight ratio of the synergist component (b) to the macrolide component (a) being greater than 1;

Such tags in which the avermectin can be an avermectin aglycone, an avermectin/milbemycin class derivative of the avermectin or aglycone, or a combination thereof; and/or in which the synergist component comprises piperonyl butoxide;

Articles capable of controlling pests of domestic animals, the articles including a pesticidally effective amount of an active ingredient composition, impregnated in a polymer resin base from which it can be released, which composition contains: (a) a macrolide component comprising a pesticidal compound of the avermectin-milbemycin class; and (b) a synergist component comprising a synergist compound; with (c) the weight ratio of the synergist component (b) to the macrolide component (a) being greater than 1;

Such articles in the form of a tag, collar, band, film, or adhesive strip or patch.

Such articles in which the macrolide component comprises an avermectin; those in which the avermectin can be an avermectin aglycone, an avermectin/milbemycin class derivative of the avermectin or aglycone, or a combination thereof;

Such articles in which the synergist component comprises an aryl aliphatic ether-class synergist compound; those in which the aryl aliphatic ether-class synergist compound comprises any of the 1,3-benzodioxole synergist compounds or combinations thereof, such as piperonyl butoxide, piprotal, sesamex, sesamolin, piperonyl sulfoxide, bucarpolate, safrole, isosafrole, piperine, myristicin, apiole, dillapiole, dihydrodillapiole, or a combination thereof, e.g., piperonyl butoxide;

Active ingredient compositions capable of controlling pests of domestic animals, the compositions containing: (a) a pesticidally effective amount of a macrolide component comprising a pesticidal compound of the avermectin-milbemycin class; and (b) a synergist component comprising a synergist compound; with (c) the weight ratio of the synergist component (b) to the macrolide component (a) being greater than 1;

Such compositions in the form of a spotting solution, a soak, rub, dip, spray, dust, or other topical formulation, or is comprised by a polymeric material from which it can be released;

Such compositions in which the macrolide component comprises an avermectin; those in which the avermectin can be an avermectin aglycone, an avermectin/milbemycin class derivative of the avermectin or aglycone, or a combination thereof;

Such compositions in which the synergist component comprises an aryl aliphatic ether-class synergist compound; those in which the aryl aliphatic ether-class synergist compound comprises any of the 1,3-benzodioxole synergist compounds or combinations thereof, such as piperonyl butoxide, piprotal, sesamex, sesamolin, piperonyl sulfoxide, bucarpolate, safrole, isosafrole, piperine, myristicin, apiole, dillapiole, dihydrodillapiole, or a combination thereof, e.g., piperonyl butoxide;

Methods for controlling pest infestation of domestic animals, involving (I) providing (A) a pesticidally effective amount of an active ingredient composition containing (1) a macrolide component comprising a pesticidal compound of the avermectin-milbemycin class; and (2) a synergist component comprising a synergist compound; with (3) the weight ratio of the synergist component (b) to the macrolide component (a) being greater than 1; or (B) an article comprising a pesticidally effective amount of said composition impregnated in a polymer resin base from which it can be released; and (II) applying the composition or article to an external body surface of a domestic animal;

Such methods in which the macrolide component comprises an avermectin; those in which the avermectin can be an avermectin aglycone, an avermectin/milbemycin class derivative of the avermectin or aglycone, or a combination thereof;

Such methods in which the synergist component comprises an aryl aliphatic ether-class synergist compound; those in which the aryl aliphatic ether-class synergist compound comprises any of the 1,3-benzodioxole synergist compounds or combinations thereof, such as piperonyl butoxide, piprotal, sesamex, sesamolin, piperonyl sulfoxide, bucarpolate, safrole, isosafrole, piperine, myristicin, apiole, dillapiole, dihydrodillapiole, or a combination thereof, e.g., piperonyl butoxide;

Such methods in which the pest is an arthropod ectoparasite, such as a member of the horn flies, *Haematobia irritans irritans*, or buffalo flies, *Haematobia irritans exigua*.

A more complete appreciation of the present invention and its scope can be obtained from the following detailed description of the invention, and the appended claims.

DRAWINGS

The drawings described herein are for illustration purposes only and are not intended to limit the scope of the present disclosure in any way.

FIG. 1 presents a graph of test results for control of horn flies (*Haematobia irritans irritans*) on beef cattle using ear tags impregnated with a composition according to an embodiment hereof, versus using commercially available ear tags: ■ WARRIOR ear tag comprising the organophosphate insecticides, diazinon and chlorpyrifos; ▲ PYthon ear tag comprising the synthetic pyrethroid insecticide, zetacypermethrin, plus piperonyl butoxide; and ♦ Present Embodiment of ear tag comprising abamectin plus piperonyl butoxide.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Background Summary,") and subheadings (such as "Articles") used herein are intended only for general organization of topics within the disclosure of the invention, and are not intended to limit the disclosure of the invention or any aspect thereof. In particular, subject matter disclosed in the "Field" and "Background" may include aspects of technology within the scope of the invention, and may not constitute a recitation of prior art. Subject matter disclosed in the "Summary" is not an exhaustive or complete disclosure of the entire scope of the invention or any embodiments thereof.

The citation of references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references. All references cited in the Description section of this specification are hereby incorporated by reference in their entirety.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations of the stated features. Specific Examples are provided for illustrative purposes of how to make, use and practice the compositions and methods of this invention and, unless explicitly stated otherwise, are not intended to be a representation that given embodiments of this invention have, or have not, been made or tested.

In accordance with a preferred embodiment of the present invention, an effective amount of at least one avermectin or milbemycin, such as, but not limited to abamectin, ivermectin, milbemectin, is employed as a topically applied active ingredient composition. In accordance with a highly preferred embodiment of the present invention, a mixture of at least one avermectin, such as, but not limited to ivermectin or abamectin, and a synergist, such as, but not limited to piperonyl butoxide (preferably technical grade) in ratios of about one part ivermectin or abamectin and about at least two parts piperonyl butoxide, is provided as a synergized active ingredient composition. Such a combination has been found to exhibit a surprisingly high level of effectiveness against pest infestations of animals, including cattle and other livestock. In particular, effectiveness has been found against various ecdysozoan pests, e.g., arthropod parasites.

The synergized active ingredient compositions of the present invention demonstrate a surprising increase in contact toxicity against *Haematobia irritans* species (e.g., horn flies and buffalo flies) and other domestic animal ectoparasites, including populations resistant to pyrethroids and organophosphates, making it more feasible to utilize avermectins such as ivermectin or abamectin, or milbemycins such as milbemectin, in formulations for long-lasting control of these pests. Examples of other ecdysozoan pests, e.g., ectoparasites, that may be controlled thereby include various lice, mites, and keds, and other species.

Synergized active ingredient compositions according to the present invention exhibit oil solubility and releasability from a resin base. The resin base can form an animal tag, such as an ear tag or a hang tag. Such ear tags have been unexpectedly found to provide, through the small amount of contact between the tag and the animal's skin, a sufficient dose of the avermectin or milbemycin to effectively treat parasitic insect infestations.

Avermectins and Milbemycins

Members of the avermectin/milbemycin class of compounds act by interfering with gamma aminobutyric acid (GABA), a neurotransmitter that is only found as a peripheral neurotransmitter in invertebrate pests, e.g., insects, but that in mammals is found only in the brain. Specifically, compounds of this class, such as abamectin, ivermectin, and milbemectin, have been found to bind selectively with strong affinity to GABA-gated, glycine-gated, or glutamate-gated chloride ion channels which occur in invertebrate nerve and muscle cells. This leads to increased permeability of the cell membranes to chloride ions which leads to hyperpolarization of the nerve or muscle cell, resulting in paralysis and eventual death of the pest.

The naturally occurring avermectins and milbemycins are 16-member macrolides containing a spiro-ketal group: the 16-member core macrocycle is fused to a 6,6-spiroketal group and is also separately fused to a further additional ring or ring system that is a single ring (a cyclohexene or benzene ring) or a bi-cyclic ring system (a hexahydrobenzofuran ring system); the core macrocycle of these compounds further comprises a conjugated diene. The resulting tetra- or pentacyclic unit can be isolated in a glycone form, from various *Streptomyces* spp. cultures. These features are illustrated in formula (1).

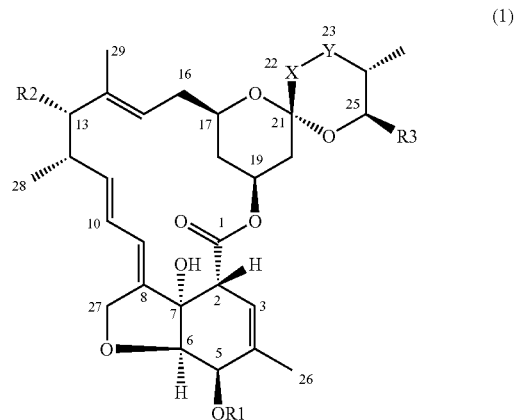

(1)

A number of exemplary members of the avermectin-milbemycin group, which are useful in various embodiments hereof, are shown in Table 1, with reference to formula (1).

TABLE 1

Exemplary Avermectin-Milbemycin Group Members

| NAME | X-Y | —OR1 | R2 | R3 | Notes |
|---|---|---|---|---|---|
| Avermectin A1a | CH=CH | —OCH$_3$ | [O]2 | sec-Butyl | |
| Avermectin A1b | CH=CH | —OCH$_3$ | [O]2 | iso-Propyl | |
| Avermectin A2a | CH$_2$—CH(OH) | —OCH$_3$ | [O]2 | sec-Butyl | |
| Avermectin A2b | CH$_2$—CH(OH) | —OCH$_3$ | [O]2 | iso-Propyl | |
| Avermectin B1a | CH=CH | —OH | [O]2 | sec-Butyl | Abamectin (~80%) |

TABLE 1-continued

Exemplary Avermectin-Milbemycin Group Members

| NAME | X-Y | —OR1 | R2 | R3 | Notes |
|---|---|---|---|---|---|
| Avermectin B1b | CH=CH | —OH | [O]2 | iso-Propyl | Abamectin (~20%) |
| Avermectin B2a | $CH_2$—CH(OH) | —OH | [O]2 | sec-Butyl | |
| Avermectin B2b | $CH_2$—CH(OH) | —OH | [O]2 | iso-Propyl | |
| Avermectin H2B1a | $CH_2$—$CH_2$ | —OH | [O]2 | sec-Butyl | Ivermectin (~80%) |
| Avermectin H2B1b | $CH_2$—$CH_2$ | —OH | [O]2 | iso-Propyl | Ivermectin (~20%) |
| Doramectin | CH=CH | —OH | [O]2 | Cyclohexyl | |
| Selamectin | $CH_2$—$CH_2$ | =NOH | [O] | Cyclohexyl | |
| Emamectin B1a | CH=CH | —OH | M[O]2 | sec-Butyl | Emamectin (~80%) |
| Emamectin B1b | CH=CH | —OH | M[O]2 | iso-Propyl | Emamectin (~20%) |
| Eprinomectin B1a | $CH_2$—$CH_2$ | —OH | A[O]2 | sec-Butyl | Eprinomectin (~80%) |
| Eprinomectin B1b | $CH_2$—$CH_2$ | —OH | A[O]2 | iso-Propyl | Eprinomectin (~20%) |
| Milbemycin A3 | $CH_2$—$CH_2$ | —OH | H | Methyl | Milbemectin (~20%) |
| Milbemycin A4 | $CH_2$—$CH_2$ | —OH | H | Ethyl | Milbemectin (~80%) |
| Milbemycin B | $CH_2$—$CH_2$ | —$OCH_3$ | H | H | Open THF: Chxene + C8($CH_2OH$) |
| Milbemycin D | $CH_2$—$CH_2$ | —OH | H | iso-Propyl | |
| Milbemycin E | $CH_2$—$CH_2$ | —$OCH_3$ | H | iso-Propyl | Open THF: Chxene + C8($CH_2OH$) |
| Milbemycin G | $CH_2$—$CH_2$ | —$OCH_3$ | H | iso-Propyl | |
| Milbemycin A3 Oxime | $CH_2$—$CH_2$ | =NOH | H | Methyl | Milbemycin Oxime (~20%) |
| Milbemycin A4 Oxime | $CH_2$—$CH_2$ | =NOH | H | Ethyl | Milbemycin Oxime (~80%) |
| Milbemycin Alpha-2 | $CH_2$—$CH_2$ | —$OCH_3$ | H | Methyl | |
| Milbemycin Beta-1 | $CH_2$—$CH_2$ | —$OCH_3$ | H | Methyl | Open THF: Chxene + C8($CH_2OH$) |
| Milbemycin Beta-3 | $CH_2$—$CH_2$ | —OH | H | Methyl | Open THF: Bzene + C8($CH_3$) |
| Milbemycin K | $CH_2$—$CH_2$ | —$OCH_3$ | H | Ethyl | |
| Moxidectin | $CH_2$—C(=NOH) | —OH | H | 1,3-dimethyl-butenyl | |
| Nemadectin | $CH_2$—CH(OH) | —OH | H | 1,3-dimethyl-butenyl | |
| Lepimectin A3 | $CH_2$—$CH_2$ | —OH | MIPA | Methyl | Lepimectin (~20%) |
| Lepimectin A4 | $CH_2$—$CH_2$ | —OH | MIPA | Ethyl | Lepimectin (~80%) |

Notes:
"=NOH" indicates substitution with a hydroxyimino group; at C5 this replaces the hydroxyl or alkoxyl.
"[O]2" indicates that C13 is substituted with a di-oleandrosyl group.
"M[O]2" indicates that C13 is substituted with a 4"-deoxy-4"methylamino-di-oleandrosyl group.
"A[O]2" indicates that C13 is substituted with a 4"-deoxy-4"acetylamino-di-oleandrosyl group.
"[O]" indicates that C13 is substituted with a mono-oleandrosyl group.
"Open THF: Chxene + C8($CH_2OH$)" indicates that, compared to formula (1), the named compound has a structure equivalent to one in which the tetrahydrofuran ring of the depicted fused hexahydro-benzofuran system is opened, leaving a fused cyclohexene ring of C2-C7 and, at C8, a hydroxymethyl substituent.
"Open THF: Bzene + C8($CH_3$)" indicates that, compared to formula (1), the named compound has a structure equivalent to one in which the tetrahydrofuran ring of the depicted fused hexahydro-benzofuran system is opened and deoxidated, and that the fused component is also tetradehydro, thereby leaving a fused benzene ring of C2-C7 and, at C8, a methyl substituent.
"MIPA" indicates that C13 is substituted with a [(methoxyimino)phenylacetyl]oxy group.

In naturally occurring or commonly prepared avermectin compound a/b pairs, e.g., mixed avermectin B1a/B1b pairs, and derivatives of such mixed pairs, e.g., ivermectin, the ratio (a:b)>1 is typically found, with the larger compound being the major component. In naturally occurring or commonly prepared milbemcyin compound pairs, e.g., mixed milbemectin A3/A4 pairs, and derivatives of such mixed pairs, e.g., milbemycin oxime, the ratio (A4:A3)>1 is typically found, with the larger compound being the major component. Approximately 80:20 ratios are common and are useful herein in some embodiments; in some embodiments, a composition comprising such compounds in at least a 60:40, 70:30, 75:25, or 80:20 ratio can be used.

The avermectins are a series of compounds possessing anthelmintic and antiparasitic activity that include both naturally occurring compounds as well as derivatives and analogs that were developed based on the structures of the original avermectin natural products. These natural products were first isolated as a complex from a fermentation broth of an actinomycete strain, *Streptomyces avermitilis*, and described in U.S. Pat. No. 4,310,519 to Albers-Schonberg et al., the entire specification of which is incorporated herein by reference. The naturally occurring avermectin complex includes four closely related major components, designated A1a, A2a, B1a, and B2a, and four minor components, designated A1b, A2b, B1b, and B2b, which are respectively lower homologs of the corresponding major components.

Such naturally occurring avermectin-type compounds are typically found in their glycone form, being glycosylated at C13; and the most common glycosylation thereof is C13 linkage to a dioleandrosyl group: alpha-L-oleandrosyl-1"-O→4'-alpha-L-oleandrosyl-1'-O-yl. The B1a/B1b avermectins are the most preferred pair with respect to antiparasitic applications, and an approximately 80:20 mixture thereof is known as abamectin. Some avermectins have been produced as 22,23-dihydro derivatives, such as those described in U.S. Pat. No. 4,199,569 to Chabala et al., the entire disclosure of which is incorporated herein by reference. In some embodiments in which a 22,23-dihydro avermectin is used, 22,23-dihydro avermectin B1a or B1b can be used; in some such embodiments, a combination, e.g., an approximately 80:20 mixture, of both of these compounds can be used. Such a mixture is also known as ivermectin. Similarly, milbemycins include natural products and derivatives thereof that are based on such naturally occurring structures; and 80:20 A4:A3 ratios of compound pairs, e.g., milbemectin, milbemycin oxime, and lepimectin, are also considered useful in some milbemycin-containing embodiments hereof.

Thus, both naturally occurring avermectins and milbemycins, and biotransformed or semisynthetic derivatives of these compounds, as well as synthetic compounds having structures equivalent thereto, all of which belong to the avermectin-milbemycin class and exhibit antipest activity, are useful in various embodiments hereof. For example, milbemycin B-41D, milbemycin J, latidectin, O-demethyl selamectin; hydroxyl-selamectin, alpha- and beta-milbemycins, and milbemycin glycones can be used.

New avermectin and milbemycin derivatives can be prepared by modification of an already existing avermectin or milbemycin compound, such as by enzymatic modification, e.g., microbial biotransformation, or by chemical modification thereof. Such compounds, which exhibit antipest activity, are useful in various embodiments of the present invention. Various derivatives include those described in, e.g., U.S. Pat. No. 4,831,016 to Mrozik et al., U.S. Pat. No. 4,916,120 to Roben et al., U.S. Pat. No. 4,927,847 to Dutton et al., U.S. Pat. No. 4,945,105 to Sato et al., U.S. Pat. No. 5,008,191 to Okazaki et al., U.S. Pat. No. 5,015,630 to Fisher et al., U.S. Pat. No. 5,023,241 to Linn et al., U.S. Pat. No. 5,030,622 to Mrozik et al., U.S. Pat. No. 5,055,454 to Blizzard et al., U.S. Pat. No. 5,055,596 to Baker et al., U.S. Pat. No. 5,077,308 to Blizzard, U.S. Pat. No. 5,089,480 to Gibson et al., U.S. Pat. No. 5,114,930 to Blizzard et al., U.S. Pat. No. 5,122,618 to O'Sullivan, U.S. Pat. No. 5,169,839 to Linn et al., U.S. Pat. No. 5,177,063 to Meinke, U.S. Pat. No. 5,208,222 to Meinke et al., U.S. Pat. No. 5,240,915 to Rosegay, U.S. Pat. No. 5,262,400 to Chu et al., U.S. Pat. No. 5,350,742 to Meinke et al., U.S. Pat. No. 5,411,946 to Newbold et al., U.S. Pat. No. 5,478,929 to Arison et al., U.S. Pat. No. 5,556,868 to Banks, U.S. Pat. No. 5,614,470 to Takeshiba et al., U.S. Pat. No. 5,830,875 to Mrozik et al., U.S. Pat. No. 5,840,704 to Gibson et al., U.S. Pat. No. 5,883,080 to Dutton et al., U.S. Pat. No. 5,981,500 to Bishop et al., and U.S. Pat. No. 6,605,595 to Omura et al. The derivatives of the macrocylic ring systems described therein can be used in various glycone or aglycone embodiments hereof, and the derivatives of the oleandrosyl or other glycosyl moieties thereof can be independently used in various glycone embodiments hereof.

Useful derivatives in the avermectin-milbemycin class include those 16-member macrolides in which the fused benzofuran, benzene, or cyclohexene ring is replaced with another fused, homo- or hetero-hydrocarbon cycloatiphatic or aromatic ring or fused ring system having from 3 to about 8 ring carbon atoms (single ring) or from about 6 to about 15 ring carbon atoms (fused ring systems); in various embodiments, such fused ring systems can contain up to 5, preferably up to 4, or 3 or 2 fused rings. Rings and fused ring systems can be cycloaliphatic or aromatic. Useful avermectin-milbemycin derivatives also include those 16-member macrolides in which the fused 6,6-spiroketal ring system can be replaced with another spiro ring system, such as another 6,6-spiro or a 6,5-, a 5,6-, or a 5,5-spiro system. Some preferred examples of spiro ring systems include spiroether, spiroester, or spirolactone (e.g., spirolactide) ring systems, with those systems that contain two or at least two oxa ring atoms, preferably at least one oxa per ring or preferably at most 2 oxas per ring, being considered particularly useful. Spiro(bis)ether ring systems, such as spiroketal or spiroacetal ring systems, preferably 6,6-spiro(bis)ethers, can be used. In some embodiments, both the fused benzofuran/benzene/cyclohexene ring can be replaced and the fused spiroketal ring system can be replaced, as described. The resulting derivatives have so far been described in terms of aglycone forms of such avermectin-milbemycin class members. Yet, glycones and other substituted variants of these polycyclic aglycones are also useful hereon.

Examples of substituted variants of aglycones hereof are those that comprise any one or more of the following substituents: hydroxy, alkoxy, acyloxy groups; hydroxy-, alkoxy-, acyloxy-alkyl groups; hydroxyimino (i.e. oxime), alkoxyimino groups; oxo; sulfur-containing (thia or thio) analogs of the foregoing groups; halo groups; and nitrogen-containing groups, e.g. amino, cyano, imino, amido, or imido groups, alkyl-amino, -imino, -amido, or -imido groups.

Referring to formula (1), in some embodiments hereof, —OR1 can comprise 6 or fewer carbon atoms, and in some embodiments can be hydroxy, methoxy, ethoxy, hydroxyimino, methoxyimino, or ethoxyimino, with hydroxy, methoxy, and hydroxyimino being considered particularly useful in some embodiments. Also, referring to formula (1), R3 can be a C1 to C8 alkyl substituent in various embodiments, preferably a methyl, ethyl, propyl, propenyl, butyl, or butenyl group or a saturated or unsaturated cyclic group.

In various embodiments, the aglycone or substituted aglycone moiety of the compound can also have a saccharide substituent. A saccharide substituent can be a mono- or polysaccharide; among polysaccharide substituents, di-, tri-, and tetra-saccharides are preferred, and di- and tri-saccharides are considered particularly useful is some embodiments. In various embodiments, mono- and di-saccharides are particularly preferred. A saccharide substituent can be attached at C13, or at another position; C13 is a preferred location for glycosylation in glycosylated compounds hereof. In various embodiments, an aglycone or substituted aglycone can contain one or more saccharide substituents, with singly glycosylated compounds being preferred glycosylated compounds for use herein.

Monosaccharide residues of a saccharide substituent can be any of: the aldo- or keto-hexoses, -pentoses, -tetroses, or -heptoses, with hexoses and pentoses being considered particularly useful, and hexoses particularly preferred, in some embodiments; or deoxy cognates thereof. In some embodiments of glycones, monosaccharide residues of the saccharide substituent can be modified monosaccharide residues, i.e. saccharides having as substituents, e.g.: alkyl, alkoxy, acyl, acyloxy groups; alkoxy-, acyl-, acyloxy-alkyl groups; oxo; sulfur-containing (thia or thio) analogs of these; or organic nitrogen-containing groups, e.g. amino, imino, amido, or imido groups, alkyl- or acyl-amino, -imino, -amido, or -imido groups, and the like. In various embodiments, non-sulfur-containing monosaccharide residues are preferred. In some embodiments, a compound for use herein can contain a mono- or di-oleandrosyl substituent at C13 of the aglycone moiety; in some embodiments, the oleandrosyl substituent can be a modified oleandrosyl saccharide group. Other specific examples of useful monosaccharide residues include olivose, cladinose, and desosamine. In some embodiments of di- and greater saccharides, the monosaccharide residues thereof can be the same or different.

Specific examples of aglycone substitutions found in some avermectins or milbemycins include, e.g.: C5 substitution with hydroxylimino, alkoxy, oxo, or alkoxylimino group(s); C13 substitution with hydroxy, alkoxy, or acyloxy group(s), hydroxy-, alkoxy-, or acyloxy-alkyl group(s); mono- and poly-saccharides including amino sugars, alkylamino sugars, acylamino sugars, and the like; or C13 substitution with other cyclic groups, e.g., aryl-acyl and aryl-acyloxy groups, such as 2-[4-(2-alkyoxy acetamido)phenyl]-cyclopentanoyloxy groups; C23 substitution with hydroxy, hydroxylimino groups; C26 substitution with alkoxy groups, e.g., 3-methyl-2-butenoyloxy; C27 substitution with oxo or halo, e.g., fluoro; C28 substitution with hydroxy; and C29 substitution hydroxy or dihydroxy.

In the above substituent groups for the aglycone, "alkyl" refers to any (homo- or hetero-) aliphatic and/or cycloaliphatic group, preferably containing 18 or fewer carbon atoms, or 15, 12, 10, 8, or 6 or fewer carbon atoms. Similarly, "acyl" in regard to such substituents refers to radicals of carboxylic acids comprising such an alkyl group attached to a carbonyl carbon of the acid. Esters of acid, e.g., acyl, groups present in a compound hereof can be provided in the form of alkyl esters thereof. Compounds hereof can likewise be provided in the form of a salt in various embodiments. Epimers of a member of the avermectin-milbemycin class are also useful herein, e.g., C12-epi or C13-epi compounds.

Compounds hereof also include the physiologically acceptable salts and complexes of avermectin-milbemycin class compounds, such as any of the acid addition or other salts that are commonly used in veterinary or human pharmaceutical practice. These include, e.g., aromatic and aliphatic mono-, di-, and tri-carboxylic acids, such as amino acids, benzoates, acetates, etc., and those described in P. H. Stahl and C. G. Wermuth, editors, *Handbook of Pharmaceutical Salts: Properties, Selection and Use* (2002) (Wiley-VCH/VHCA, Weinheim/Zürich), and those otherwise known in the art. Thus, e.g., emamectin-benzoate can be used in various embodiments hereof.

In various embodiments, compounds of the avermectin-milbemycin class, including avermectin/milbemycin derivatives, can have an octanol-water partitioning coefficient (logPow) value that is about 3.5 or more, or about 4 or more; in some embodiments at least 3.5 or at least 4; and preferably more than 4. In some embodiments, the logPow value can be about 8 or less. Such logPow values can be assessed by an analytical chemistry technique, or estimated using, e.g., QSAR algorithm calculations. Calculated logPow value estimates can be performed, e.g., using a publicly available program such as the ALOGPS software available on-line at the World Wide Website (.vcclab.org/lab/alogps/) of the Virtual Computational Chemistry Laboratory of the Institut für Bioinformatik of the GSF-Forschungszentrum für Umwelt und Gesundheit, GmbH (Munich, Del.). Any analytical chemistry method known for determining logPow values greater than zero can be used, such as by analysis at about pH7.2, at room temperature or about 25° C., according to a procedure such as is described, e.g., in U.S. Pat. No. 7,074,785 to Seitz et al., or in ASTM E1147-92, or by a shake-flask (or tube) phase separation method using an equilibrated water-octanol system.

In various embodiments, compounds of the avermectin-milbemycin class, including avermectin/milbemycin derivatives, can have a molecular weight from about 400 to about 2500. In various embodiments, compounds of the avermectin-milbemycin class, including avermectin/milbemycin derivatives, comprise a polycyclic macrolide aglycone moiety that has a molecular weight of about 1500 or less, 1200 or less, 1000 or less; of about 400 or more, 500 or more, 600 or more, or 700 or more; and in various preferred embodiments from about 450 to about 900, about 450 to about 800, 450 to about 700, or about 450 to about 600. In various embodiments in which the aglycone is substituted, the compound can have a molecular weight of at least or about 450, 500, 550, or 600; of about 2500 or less, or less than or about: 2250, 2000, 1750, 1500, 1250, or 1000. In some preferred embodiments, the compound can have a molecular weight of about 450 to about 1000.

Many types of pesticidal derivatives of the avermectins and milbemycins that fall within the avermectin/milbemcyin class of pesticides are described in scores of patent documents and many more journal articles; these are also useful in various embodiments of the present invention.

Pesticidal activity of a given derivative can be assessed by use of any method known in the art, such as by exposing sets of arthropod adults or larvae to the compound at one or more concentration level(s) and determining the number of survivors compared to untreated controls. Rapids methods such as those described in U.S. Pat. No. 5,583,008 to Johnson et al., can be used.

In various embodiments, an avermectin can be used in or as the macrolide component of the (synergized) active ingredient composition. In some embodiments, this can be any one or more of: avermectin A1a, avermectin A1b, avermectin A2a, avermectin A2b, avermectin B1a, avermectin B1b, avermectin B2a, or avermectin B2b; aglycones thereof; avermectin/milbemycin class derivatives of any of these; and combinations of the foregoing. In some preferred embodiments, the avermectin can comprise a combination of avermectin B1a and avermectin B1b or an avermectin/milbemycin class derivative or combination of avermectin/milbemycin class derivatives thereof, preferably in which the weight ratio of avermectin B1a or the B1a-derivative to avermectin B1b or the B1b-derivative is greater than 1. Among the avermectins, abamectin and ivermectin are considered particularly useful. In some preferred embodiments, the macrolide component can comprise abamectin.

One or more than one pesticidal macrolide hereof can be used in some embodiments of the present invention. In some embodiments other pesticidal active(s) can also be included. Combinations of pesticidal macrolides useful herein include the mixed a/b avermectins, the mixed A3/A4 milbemycins, avermectin/milbemycin combinations, and others, e.g., those described in U.S. Pat. No. 4,560,677 to Dybas.

Synergists

As noted above, active ingredient compositions here comprise both a macrolide component and a "synergist." In the field of pest control, synergists are a class of compounds that can enhance the pesticidal activity of the pesticidal composition, in some cases by exerting an independent pest toxifying effect, by inhibiting a pesticide-degrading enzymatic activity of the pest, or by some other route.

A wide variety of pesticide synergist compounds of different chemical classes are known and these include, e.g.:

1. The alkynylpolyarene synergists, such as C2-C6 alkynyl-anthracenes, -pyrenes, -flavones, -biphenyls, and the like, see, e.g., J. G. Scott et al., *Pesticide Biochem. & Physiol.* 67:63-71 (2000);

2. The substituted N-aromatyl imines, such as 1-(1-((4-Chloro-2-(trifluoromethyl)phenyl)imino)-2-propoxyethyl)-1H-imidazole (Triflumizole);

3. The dicarboximide synergists, such as N-(2-ethylhexyl)-8,9,10-trinorborn-5-ene-2,3-dicarboximide, n-octyl bicycloheptene dicarboximide;

4. The aryl alkylamine ether and ester synergists, such as 2-((4,6-dichloro-2-biphenylyl)-oxy) triethylamine, 2-(diethylamino)ethyl 2,2-diphenyl pentanoate;

5. The aminopyridine synergists, such as 2-aminopyridine, 3-aminopyridine;

6. The organothiocyanate synergists, such as p-nitrobenzyl thiocyanate;

7. The organophosphoxy ester synergists, preferably non-insecticidal members, such as (1) organic thiophosphates, e.g., O-(4-bromo-2-chlorophenyl) O-ethyl S-propyl phosphorothioate (Profenofos); (2) organic phosphonothionates, e.g., O-ethyl-O-p-nitrophenyl phenylphosphonothionate (EPN); (3) organic phosphorothioates (carbamates), preferably non-insecticidal carbamates; and (4) trisubstituted aliphatic and aromatic phosphates, e.g., tri-o-cresyl phosphate (TOCP), triphenyl phosphate (TPP), S,S,S-tributylphosphorotrithioate (DEF), O,O-disopropyl-S-benzylthiophosphate (IBP);

8. The bis(polyhalogenated aliphatic) ether synergists, e.g., 2,3,3,3,2',3',3',3'-octachlorodipropyl ether (S-421);

9. The aryloxyalkylamine synergists, such as 3-diethylaminoethyl diphenylpropylacetate;

10. The formamidine synergists, such as N'-(2,4-dimethylphenyl)-N-[[(2,4-dimethylphenyl)imino]methyl]-N-methylmethanimidamide (Amitraz); N-(2-(4-chloro toluenyl)-imine (Chlordimeform);

11. The plant oil synergists, e.g.: sesame, neem, castor, soybean, coconut, canola, mustard, palm, citronella, and karanj (Pongamia pinnata seed) oils;

12. Various substituted aryl alcohol, acid, and ester synergists, such as 1,1-di(p-chlorophenyl)-2,2,2-trifluoroethanol (F-DMC); (1,1-bis(4-chlorophenyl)ethanol (Chlorofenethol; BCPE); diethyl maleate (DEM); and [(5-chloro-8-quinolinyl)oxy]acetic acid, 1-methylhexyl ester; and 13. The aryl aliphatic ether synergists, i.e. aliphatic ethers of aryl or alkylaryl rings.

Among this wide spectrum of synergists, the aryl aliphatic ether synergist class has been unexpectedly found to substantially enhance the contact activity of pesticidal avermectin/milbemycin class macrolide compounds. As a result, an active ingredient composition hereof preferably contains an aryl aliphatic ether synergist.

Examples of useful aryl aliphatic ether-class synergists herein include the methylenedioxyarene and the alkynyloxyarene types. Representative examples of these synergist types are set forth below.

A) Methylenedioxyarene synergists, e.g., methylenedioxynaphthalene and methylenedioxyphenyl (MDP) synergists, preferably MDP synergists; examples of methylenedioxyarene synergists including (1) benzodioxole synergists, such as 5-[2-(2-butoxyethoxy)ethoxymethyl]-6-propyl-benzodioxole (Piperonyl butoxide); 5-(bis[2-(2-butoxyethoxy)ethoxy]methyl)-benzodioxole (Piprotal); 5-(1-[2-(2-ethoxyethoxy)ethoxy]ethoxy)-benzodioxole (Sesamex); 5-[4-(benzodioxol-5-yloxy)tetrahydro-1H,3H-furo[3,4-c]furan-1-yl]-benzodioxole (Sesamolin); 5-[2-(octylsulfinyl)propyl]-benzodioxole (Sulfoxide; piperonyl sulfoxide); 2-(2-butoxyethoxy)ethyl piperonylate (Bucarpolate); 5-(2-propenyl)-benzodioxole (Safrole); 5-(1-propenyl)-benzodioxole (Isosafrole); 1-[5-(benzodioxol-5-yl)-1-oxo-2,4-pentadienyl]piperidine (Piperine); 4-methoxy-6-(2-propenyl)-benzodioxole (Myristicin); 4,7-dimethoxy-5-(n-prop-2-enyl)-benzodioxole (Apiole); 4,5-dimethoxy-6-(n-prop-2-enyl)-benzodioxole (Dillapiole); 5-(n-propyl)-6,7-dimethoxy-benzodioxole (dihydrodillapiole); (2) methylenedioxynaphthalene synergists, such as dipropyl 5,6,7,8-tetrahydro-7-methylnaphtho[2,3-d]-dioxole-5,6-dicarboxylate (Propyl isome); and 2,3-methylenedioxynaphthalene; and (3) alkynyl- and alkynyloxy-methylenedioxyarene synergists, preferably alkynyl- and alkynyloxy-methylenedioxyphenyl synergists, preferably in which the alkynyl group(s) is a C2-C6 alkynyl group (preferably at least C3, preferably up to C4; preferably those in which the alkynyl group is or comprises a 2-yne or 3-yne), such as alkynyloxy benzodioxoles, e.g., 5-[(2-butynyloxy)-isopropyl]benzodioxole (Verbutin). (Where benzodioxole is referred to herein, it is preferably 1,3-benzodioxole.)

B) Alkynyloxyarene synergists, preferably C2-C6 alkynyloxyarene synergists (preferably at least C3, or up to C4, and particularly C3), preferably those in which the alkynyl group is or comprises a 2-yne or 3-yne, such as: (1) substituted phenyl-oxy-2-alkynyl ethers, e.g., 2,6-Dichlorobenzyl-2-propynyl ether, 2,3,6-trichloro-3(2-propynyloxy)benzene (TCPB), 2-propynyl-4-chloro-2-nitrophenyl ether, O-n-Propyl-O-(2-propynyl)phenylphosphonate; (2) N-alkynyloxy imines and imides comprising aromatic ring(s), e.g., N-(propargyloxy) phthalimide; and (3) others, see, e.g., U.S. Pat. No. 6,320,085, and US Publication No. 2005/038082A1.

An ether group of such ethers can comprise an oxo-ether or thio-ether linkage; in various preferred embodiments, this can be an oxo-ether linkage. Among these compounds, methylenedioxyarene synergists are considered particularly useful. In various embodiments, the synergist can be any one or more of the methylenedioxyphenyl or methylenedioxynaphthalene synergists. In various embodiments, a methylenedioxyphenyl synergist can be used; in some preferred embodiments, this can be a benzodioxole synergist, preferably a 1,3-benzodioxole synergist. Useful examples of 1,3-benzodioxole synergist include, e.g., piperonyl butoxide, piprotal, sesamex, sesamolin, piperonyl sulfoxide, bucarpolate, safrole, isosafrole, piperine, myristicin, apiole, dillapiole, dihydrodillapiole, and combinations thereof. In some embodiments, the synergist component can comprise piperonyl butoxide (PBO). PBO can be provided in the form of pure PBO or in the form of, e.g., PBO "technical grade" which contains about 90% by weight PBO.

In various embodiments, alkyl/aliphatic group(s) of a synergist can comprise from 1 to about 18 carbon atoms. In various embodiments, aryl group(s) of a synergist can comprise from 3, 4, 5, or 6 to about 18 carbon atoms.

Active Ingredient Compositions

An active ingredient composition hereof comprises both a macrolide component and a "synergist." The compound(s) of each of these components can be mixed together to form the composition, or these compounds can be independently added to another component, e.g., a particle for use in preparing a dust, an organic solvent for use in preparing a spotting or other solution; or a resin or other matrix material. Examples of useful solvents include isopropanol and other alkyl alcohols, and organic solvents at least as hydrophobic as isopropanol, examples of which include topically acceptable: oils, e.g., biological oils, petroleum-derived oils (e.g., mineral oil), synthetic oils; polyols (e.g., glycols); polyol ethers (e.g., glycol ethers); and the like; and mixtures thereof with one another and/or with other organic solvent compound(s). Additions can be made in any order.

In some preferred embodiments, the macrolide(s) and synergist(s) can be mixed together directly, or with an organic solvent, to form the active ingredient composition. In various embodiments, such an active ingredient composition can be added to or combined with a particle or resin or other matrix material. Regardless of the nature of a composition produced for animal contact, the components thereof will preferably be selected to be veterinarily acceptable for the intended use on or in the subject animal. Spotting solutions are also referred to as "spot-on" compositions that can provide effective pesticidal protection by application to a single spot or line on the subject animal, e.g., on the back between the shoulder blades or along the spine. Such point-of-contact formulations are topically applied to less than 10% of the subject animal's body surface area, preferably less than 5%, or about 2% or less, or about 1% or less; and typically about or at least 0.1% of the surface area, or about or at least 0.2% or 0.5%. These are distinguished from general topical formulations that are intended to cover about 25-50% or more of the body surface area of the animal, e.g.: soaks, dips, rubs, sprays, and pour-on formulations.

In various embodiments of an active ingredient composition, the ratio of the concentrations by weight of the synergist component to pesticidal macrolide component can be greater than 1. In some embodiments, the ratio can be at least about 1.5:1, 2:1, or 2.5:1. In some embodiments, the ratio can be from about 2:1 up to about 10:1 or up to about 5:1. In some embodiments, weight ratios of about 1.5:1 to about 2.5:1 are preferred, with about 2.25:1 being considered particularly useful; these ratios are considered especially useful for glycone macrolide-containing compositions. In some embodiments of aglycone macrolide-containing compositions, weight ratios of about 2.5:1 to about 4:1 are preferred, with about 3.5 being considered particularly useful.

In some embodiments, an active ingredient composition hereof can include pest attractant(s), pest juvenilizing hormone(s), and/or other pest-affective substance(s); dyes, pigments, colorants; chelants, anti-oxidants; fragrance; and/or skin-benefit agents such as vitamins, emollients, waxes, and the like. Fragrance can be provided by inclusion of essentially oils, e.g., orange oil, lemon oil, etc., or by inclusion of a terpene such as D-limonene or a fragrant ester. In some embodiments, an active ingredient composition hereof can include an animal licking- or chewing-aversion agent, e.g., a bitter-tasting component such as quinine or denatonium benzoate or a pain-inducing component such as capsaicin.

Resin-Based Articles

As noted above, point-of-contact pesticide technologies include impregnated ear tags, impregnated "hang-tags" attached to another unit such as an identification tag or halter, and spotting compositions such as spotting solutions, and also includes, e.g., pesticide-impregnated: identification medallions or badges, pesticide-impregnated collars, bands, films, strips, or patches, and pesticide-delivering adhesive strips or patches, and the like.

In various preferred embodiments, an active ingredient composition of the present invention can be present within, e.g. impregnated into, a polymeric material, from which the active ingredient composition can be released. Such a polymeric material, referred to herein in various embodiments as a "resin base," can be shaped in the form of an article, e.g., an ear tag, from which the active ingredient composition can be released. Other examples of such articles include hang tags, medallions, badges, collars, bands, films, and adhesive strips or patches. The polymeric material/resin base can comprise a plastic or elastic (e.g., rubber) as the body of the article, which material serves a matrix from which the release can take place. The impregnation can be accomplished by any number of suitable means, such as, but not limited to co-extrusion or compounding; though in some embodiments, a polymer material or article can be contacted with an active ingredient composition to permit it to absorb the composition. The resin base is capable of allowing the active ingredient composition, or at least pesticidal macrolide(s) thereof, to be released. Preferably, the resin base is capable of allowing the pesticide compositions to be slowly released from the resin base over an extended period of time, such as several months. Preferably, the impregnated resin base is substantially odorless.

The impregnated resin base is formed by suitable means, such as injection molding or profile extrusion and stamping processes, into a desired shape such as, but not limited to an ear tag. The exact shape and dimensions of the ear tag are not thought to be critical to the success of the present invention. Instead, in the case of such an ear tag or similar article, an important feature is that the ear tag is able to touch the subject animal's skin (epidermis and/or epidermal hair) by point-of-contact so as to permit the insecticide composition to be applied to the animal. The ear tag is preferably fastened to at least one of the animal's ears in any number of conventional ways. In one preferred embodiment, the ear tag can be fastened to either the front or the back of the ear by attachment to an inert, polyurethane, male button that is used to pierce the ear of the animal.

The resin base employed can be thermosetting or thermoplastic, although the latter is more readily employed in the manufacture of an ear tag of the present invention. Examples of suitable substances are polyolefins (e.g., polyethylene, polypropylene and copolymers of ethylene and propylene); halogenated polyolefins (e.g., chlorinated polyethylene); polyacrylates (e.g., polymers and copolymers of methyl acrylate, ethyl acrylate, methyl methacrylate and ethyl methacrylate); polymers of vinyl compounds (e.g., polystyrene and polymerized divinylbenzene); polyvinyl halides (e.g., polyvinyl chloride); polyvinyl acetals (e.g., polyvinyl butyryl); polyvinylidene compounds (e.g., polyvinylidene chloride); synthetic and natural elastomers (e.g., rubber obtained from *Hevea brasiliensis*), cis-1,4-polyisoprene, acrylonitrile-butadiene copolymers, polybutadiene styrene-butadiene copolymer (SBR); urea-formaldehyde and melamine-formaldehyde resins; epoxy resins (e.g., polymers of polyglycidyl ethers of polyhydric phenols); cellulose plastic (e.g., cellulose acetate, cellulose butyrate and cellulose nitrate); and polyurethanes. It should be noted that the choice of the resin base will depend both on the particular active ingredient mixture with which it is to be formulated and the conditions under which the final formulation will be employed. To exhibit greatest pesticidal effect, the resin base is preferably insoluble in water and presents a hydrophobic surface, thus resisting the absorption of moisture on its surface which could dilute the active ingredients. In some preferred embodiments, a nitrile butadiene rubber (NBR) can be used.

Preferably, the resin base may include a polymer or a copolymer of a vinyl compound, for example, polyvinyl halides (e.g., polyvinyl chloride and polyvinyl fluoride); polyacrylate and polymethacrylate esters (e.g., polymethyl acrylate and polymethyl acrylate and polymethyl methacrylate); and polymers of vinyl benzenes (e.g., polystyrene and polymer polymerized vinyl toluene). Because it possesses desirable physical properties with desirable release rate characteristics for the insecticide, one of the preferred macromolecular substances is a polymer of vinyl chloride (e.g., PVC), which can in some embodiments be combined with an NBR or other resin modifier.

It is generally important to include a plasticizer in the resin base in order to permit satisfactory tag production by use of common commercial methods, e.g., automated manufacturing processes, although resin-based products without a plasticizer can be prepared in some embodiments hereof. Examples of plasticizers are phthalates (e.g., di(2-ethylhexyl) phthalate, diethylglycol phthalate, dioctyl phthalate, diphenyl phthalate, dicyclohexyl phthalate, dimethyl phthalate, diethyl phthalate, dihexyl phthalate, di(2-ethylhexyl) isophthalate, and di(2-ethylhexyl) hexahydrophthalate); sebacates (e.g., di(2-ethylhexyl) sebacate, dipentyl sebacate, n-butyl benzyl sebacate, dimethyl sebacate, and dibenzyl sebacate); adipates (e.g., isobutyl adipate, di(2-ethylhexyl) adipate, dicapryl adipate, dioctyl adipate and dinonyl adipate); citrates (e.g., acetyltributyl citrate and acetyl triethyl citrate); succinates; azelates; stearates; and trimellitates. Other compatible plasticizers are, for example, hydrogenated polyphenols; alkylated aromatic hydrocarbons; polyester plasticizers, for example, polyesters of polyols, such as hexanediol; polycarboxylic acids, such as sebacic or adipic acid, having molecular weights of about 2000; and epoxide plasticizers such as epoxidized soybean oil, epoxidized linseed oil and epoxidized tall oils (such as octyl epoxy tallate). Without being bound to a particular theory of the operation of the present invention, it is believed that a relatively softer resin base, as opposed to a relatively harder resin base, will enhance the delivery of the active ingredient composition when the ear tag contacts the animal's body. It is believed that higher concentrations of plasticizers, which cause a softer resin base, enable higher release rates of impregnated active ingredients. In some preferred embodiments, an epoxide plasticizer can be used.

Other materials such as dyes, pigments, colorants, fluorescents, lubricants, fillers, anti-oxidants and ultraviolet stabilizers may be included in the formulation. For example, it has been found that the stability of the formulation is extended if amounts of 0.10% to about 0.25% by weight, of each one or more suitable chemical stabilizers are included. For example, certain hydroxycinnamates (such as IRGANOX® 1076, octadecyl 3,5-di-tert-butyl-4-hydroxyhydrocinnamate) and benzotriazoles (such as TINUVIN® P, 2-(2'-hydroxy-5'-methylphenyl)benzotriazole) are effective as stabilizers against heat and ultraviolet light degradation. Further examples of useful stabilizers include: poly N-vinylpyrrolidone (PNVP); polyethylene glycol (PEG); metal salts of long chain fatty acids, e.g., zinc stearate, calcium stearate; finely divided inorganic particles, e.g., calcium carbonate, lithium-aluminum hydroxide-carbonate (see U.S. Pat. No. 5,356,567 to Tatebe et al.), or silica; and those described, e.g., in U.S. Pat. No. 3,407,171 to Jennings et al. and U.S. Pat. No. 4,269,743 to Hulyalkar et al. In some embodiments, a combination of any of these can be used. In various embodiments, hydroxycinnamate, PNVP, metal stearate, and inorganic stabilizers can be used.

In some embodiments, the formulation can include pest attractant(s), pest juvenilizing hormone(s), and/or other pest-affective substance(s). Formulations can also include animal licking- or chewing-aversion agents such as capsaicin or denatonium benzoate, to prevent animals from licking or chewing an article according to the present invention; see, e.g., U.S. Pat. No. 6,468,554.

In various embodiments, such a resin composition, containing an active ingredient composition according to the present invention, can be formed into an article, such as an ear tag or hang tag, by any conventional method known in the art, such as molding, extrusion-and-cutting, heated pressing, and the like. Granulated resin base components, e.g., granulated PVC et al., can be combined with the active ingredient composition, or its components, and the resulting combination can be formed, e.g., heated and: molded, pressed, extruded, or blow-molded to prepare an article (or part) hereof, e.g., a tag, badge, medallion, collar or band, film, adhesive strip or patch. The heating of this combination will be at a temperature below that of the point at which degradation of the components thereof begins. Examples of formation methods useful herein include those described in U.S. Pat. No. 4,721,064 to Denk et al., U.S. Pat. No. 5,294,445 to Sieveking et al., U.S. Pat. No. 4,581,834 to Zatkos et al., and U.S. Pat. No. 6,758,000 to Sandt et al. An article hereof can consist of the result of the formation process or can comprise the part resulting from the formation process and other element(s).

A tag or similar article hereof (badge, medallion, collar, etc.) can be prepared according to any desired format in which it can be affixed to the subject animal. In some embodiments, it can be prepared as single piece or multi-piece (e.g., two-piece) article in which the two pieces can interact, e.g., snap together. In some embodiments, the article, e.g., a tag, can be designed to hang from a button, stud, or post, a staple, or from a ring or collar that is to be placed around, adhered to, or pierced into or through a body feature of the subject animal, e.g., a neck or an ear; it can similarly be designed to hang from an identification tag or halter. The pesticidal article can be designed to perform one or more additional functions, e.g., as a visual identification or security tag, a remote-detectable collar, and the like.

In some embodiments, the thermoplastic resin can be cured, either before or after shaping into the final article, by use of a radiation or a free-radical curing agent, according to any method known useful therefore in the art. In various preferred embodiments, no such curing is employed during production of the article and none is applied after formation of the article. In contrast, in regard to thermosets, such a curing procedure is preferred in some embodiments hereof.

In various embodiments, a tag or other article or solution or other composition for direct application to a subject animal can comprise from about 1 to about 10% by weight of the pesticidal macrolide component; or at least about 2 or 5%; or from about 5% to about 8%. These concentration ranges are considered particularly useful for point-of-contact formulations (tags, spotting solutions); and though also useful for general topical formulations (soaks, rubs, sprays, and the like), some embodiments of such general topical compositions can contain an even lower concentration of the macrolide component, e.g., from about 0.1 to about 10% by weight.

Thus, in various embodiments of the present invention, a method for treating a subject animal can be performed in which an active ingredient composition is topically applied to the animal directly in the form of any such pour-on, spot-on, dust, spray, and the like. The direct topical application of the active ingredient compositions of the present invention can be accomplished in any number of conventional ways, such as by spraying, pouring, shaking, dropping, or blowing the active ingredient composition onto the animal's body. Once applied, the active ingredient compositions of the present invention are effective over the course of several weeks or months, depending on the formulation type, and are particularly effective against various ectoparasites of domestic animals, such as, but not limited to horn flies and buffalo flies. In various embodiments, the active composition comprising the PBO and avermectin-milbemycin compound(s) can be applied to silica, talc, or other small carrier particles in order to prepare a dust, e.g., by spraying the particles therewith.

Use of tags and similar articles and spotting solutions, dusts, and other compositions prepared according to various embodiments hereof can be effectively employed to provide a pesticidal effect against ecdysozoan pests, e.g., ectoparasites, of cattle and other livestock, including but not limited to buffalo flies, horn flies, Melophagus keds, lice (especially Anoplus lice), and mites, e.g., ear mites and scabies mites. In various embodiments, ear tags are surprisingly found to offer about 12 to 16 weeks or more of effective protection against buffalo fly and horn fly infestations, even though the tag material may have only casual intermittent or indirect contact with the skin (epidermis or hair) of the treated animal. For example, ear tags applied to cattle ears using a button of a different, non-pesticidal material (e.g., polyurethane or metal), from which the ear tag hangs, have been found effective to provide such ectoparasite-protection (data not shown).

In various embodiments hereof, it surprisingly has been found that abamectin/milbemycin-class macrocyclic pesticides are successfully delivered to livestock through an ear tag, as shown by successful control of flies and other species, by point-of-contact application, because virtually all other uses of avermectin, ivermectin, etc. are done by oral administration, by transdermal injection, or by global/general topical administration for absorption through the skin; and because these techniques depend on ingestion by the pest to kill it. Such a high level of point-of-contact activity has not been seen before in the abamectin/milbemycin-class macrocyclic pesticides. It has also surprisingly been found that the synergistic effect of piperonyl butoxide with, e.g., the avermectins, speeds up the rate of killing horn flies compared with avermectin alone.

In various embodiments hereof, epoxidized soybean oil (ESO) has also been found to have a synergizing activity in combination with abamectin/milbemycin-class macrocyclic pesticides, e.g., ivermectin, and can be used in ear tag and other articles and compositions therewith. Useful concentrations thereof could be in the same range as that described herein for PBO. In various embodiments hereof, a PBO, ESO, or other synergist as described herein can be used to enhance the bioactivity of a abamectin/milbemycin-class macrocyclic compound even if it has a non-pesticidal activity, e.g., as an antimicrobial (e.g., antibacterial, antifungal, or antiprotist), anticancer, immunomodulator, or other agent. Thus, in some embodiments, a composition hereof can be administered in order to treat, or can be co-administered to co-treat, a condition or disease other than parasite infestation.

EXAMPLES

Example 1-A

Ivermectin Toxicity

A comparison of ivermectin formulations is made to determine their toxicity to horn fly (*Haematobia irritans irritans*) strains. Three formulations are tested: ivermectin alone, ivermectin formulated with epoxidized soybean oil (ESO), and ivermectin formulated with piperonyl butoxide (PBO). Both pyrethroid-resistant (PY-Resistant) and pyrethroid-susceptible (PY-Susceptible) horn fly strains are tested. Contact toxicity is determined after four hours of exposure by contact with treated filter papers, according to the Sheppard & Hinkle resistance test method for horn flies. See D C Sheppard & N C Hinkle, "A field procedure using disposable materials to evaluate horn fly insecticide resistance," *J. Agric. Entomol.* 4:87-89 (1987). Results are summarized in Table 1.

Table 1 presents the contact toxicity results in units of $\mu g/cm^2$, computed using Log-Probit Analysis. See, e.g., V. K. Borooah, *Logit and Probit* (2002) (Sage Publications, Thousand Oaks, Calif., USA).

TABLE 1

Horn Fly Contact Toxicity of Ivermectin Alone or With Synergists

| Active Ingredient Mixture[1] | PY-Resistant | | | | PY-Susceptible | | | |
|---|---|---|---|---|---|---|---|---|
| | Lethal Concentration[2] | | Synergist Ratios[3] | | Lethal Concentration | | Synergist Ratios | |
| | $LC_{50}$ | $LC_{90}$ | $SR_{50}$ | $SR_{90}$ | $LC_{50}$ | $LC_{90}$ | $SR_{50}$ | $SR_{90}$ |
| Ivermectin | 93.8 | 478.0 | — | — | 165.6 | 418.3 | — | — |
| Ivermectin + ESO (1:2) | 58.9 | 228.7 | 4.79 | 6.28 | 39.2 | 245.3 | 12.67 | 5.12 |
| Ivermectin + PBO (1:2) | 31.2 | 76.0 | 9.02 | 18.88 | 27.6 | 78.2 | 18.01 | 16.06 |

[1] ESO = epoxidized soybean oil (added 2:1 w/w to ivermectin); PBO = piperonyl butoxide, technical (added 2:1 w/w to ivermectin)

[2] $LC_{50}$ and $LC_{90}$ = the Lethal Concentration to kill either 50% or 90%, respectively, of treated pests after 4-hour exposure.

[3] $SR_{50}$ and $SR_{90}$ = the Synergist Ratios calculated by dividing (A) the $LC_{50}$ or $LC_{90}$, respectively, of ivermectin, by (B) the product of (B1) the corresponding $LC_{50}$ or $LC_{90}$ for the mixture and (B2) the weight percent ivermectin concentration in the mixture (33.3%); i.e., for example, $SR_{50} = LC_{50(ivermectin)}/(0.333 \times LC_{50(mixture\ of\ ivermectin+synergist)})$.

These data show that, an ESO synergist formulation does increases the toxicity of the composition over ivermectin alone (an increase of about 35-75%, depending on LC measure and pesticide susceptibility), yet substitution of PBO for ESO surprisingly increases it yet another ~30-70%.

Example 1-B

Abamectin Toxicity

Further tests, similar to those of the Ivermectin tests described above, were performed using Abamectin compositions. The results are reported below in Table 2.

TABLE 2

Horn Fly Contact Toxicity of Abamectin Alone or With Piperonyl Butoxide*

| Active Ingredient Mixture | PY-Resistant | | | | PY-Susceptible | | | | PY-Susceptible versus PY-Resitant | |
|---|---|---|---|---|---|---|---|---|---|---|
| | Lethal Concentrations | | Synergist Ratios | | Lethal Concentrations | | Synergist Ratios | | | |
| (contact time) | $LC_{50}$ | $LC_{90}$ | $SR_{50}$ | $SR_{90}$ | $LC_{50}$ | $LC_{90}$ | $SR_{50}$ | $SR_{90}$ | $RR_{50}$ | $RR_{90}$ |
| (2 hour contact) | | | | | | | | | | |
| Abamectin | no mortality | | — | — | no mortality | | — | — | — | — |
| Abamectin + PBO (1:2) | 477.1 | 13,614 | — | — | no mortality | | — | — | — | — |
| Abamectin + PBO (1:4) | 52.22 | 186.5 | — | — | no mortality | | — | — | — | — |
| (4 hour contact) | | | | | | | | | | |
| Abamectin | 138.5 | 1,089 | — | — | no mortality | | — | — | — | — |
| Abamectin + PBO (1:2) | 8.00 | 11.75 | 51.99 | 278.24 | 48.96 | 88.32 | — | — | 6.12 | 7.52 |
| Abamectin + PBO (1:4) | 29.83 | 119.3 | 23.21 | 45.63 | 36.63 | 106.4 | — | — | 1.23 | 0.89 |
| (8 hour contact) | | | | | | | | | | |
| Abamectin | 1.19 | 7.60 | — | — | 37.65 | 175.16 | — | — | 31.64 | 23.05 |
| Abamectin + PBO (1:2) | 2.68 | 10.05 | 1.33 | 2.27 | 16.05 | 61.59 | 7.04 | 8.54 | 5.99 | 6.13 |
| Abamectin + PBO (1:4) | 5.58 | 10.44 | 1.07 | 3.64 | 7.45 | 15.99 | 25.27 | 54.77 | 1.34 | 1.53 |

*Results are in microgram/sq. cm computed using Log-Probit Analysis.
NOTES:
1. PBO = piperonyl butoxide, technical, added to abamectin in solution at 2 or 4 parts PBO per part abamectin.
2. PY-Resistant = horn fly strain resistant to synthetic pyrethroid insecticides.
3. PY-Susceptible = horn fly strain susceptible to synthetic pyrethroid insecticides.
4. $LC_{50}$ and $LC_{90}$ = the Lethal Concentration to kill either 50% or 90%, respectively, of treated pests after 4 hours' exposure by contact to treated filter papers using the Sheppard and Hinkle resistance test method for horn flies.
5. $SR_{50}$ and $SR_{90}$ = the Synergist Ratios calculated as the $LC_{50}$ or $LC_{90}$, respectively, of abamectin divided by the product of the corresponding $LC_{50}$ or $LC_{90}$ for the mixture and the abamectin concentration in the mixture); i.e., for the 1:2 ratio mixture, $SR_{50} = LC_{50(abamectin)}/(0.333 \times LC_{50(mixture)})$; for the 1:4 ratio mixture, SR50 = LC50 (abamectin)/(0.2 × LC50 (mixture)). RR50 and RR90, which are the resistance ratios calculated for the LCs of the PY-susceptible horn flies divided by the corresponding LCs for the PY-resistant horn flies.

These data show that, unexpectedly, it is the pyrethroid-resistant horn flies that appear to be much more susceptible to a synergized composition according to an embodiment hereof (abamectin with PBO) than are pyrethroid-susceptible horn flies. This increased susceptibility of pyrethroid-resistant horn flies to abamectin shows up in the fact that there is no mortality of PY-susceptible flies with abamectin alone or in combination with PBO at 2 hours, and they show resistance at 4 hours and at 8 hours compared with PY-resistant horn flies. Also, the PY-resistant horn flies show high susceptibility to abamectin alone after 8-hour contact. Furthermore, the increased speed of kill of abamectin in combination with PBO shows up with high synergism at 4 hours with PY-resistant horn flies but not until 8 hours with PY-susceptible horn flies. An additional benefit of the combination of PBO technical with abamectin over time (see the 8 hour contact results) is that the amount of insecticide mixture needed to kill either strain of horn flies at the $LC_{50}$ or $LC_{90}$ level begins to approach equal amounts, thus unexpectedly indicating that the PBO may be negating the effect of natural resistance of the PY-susceptible flies to abamectin.

Example 2

A comparison of pesticidal ear tags is made to determine their activity against horn flies (*Haematobia irritans irritans*) on beef cattle. Ear tags impregnated with 8% abamectin and 20% piperonyl butoxide technical, according to an embodiment hereof, are compared against commercially available: WARRIOR ear tags (40% organophosphate insecticide ear tags, available from Y-Tex Corp., Cody, Wyo., US, which are impregnated with the 30% diazinon and 10% chlorpyrifos); and PYTHON ear tags (10% pyrethroid insecticide ear tags, available from Y-Tex Corp., Cody, Wyo., US, which are impregnated with 10% zeta-cypermethrin and 20% piperonyl butoxide).

Tests are performed using two ear tags per head of cattle and treated cattle are studied for a 15-week time course, with horn fly infestation being assayed weekly. Results are depicted in FIG. 1 as: ■ WARRIOR ear tag-treated cattle; ▲ PYthon ear tag-treated cattle; and ♦ Present Embodiment ear tag-treated cattle.

These data show that, starting about 7 weeks post-treatment, cattle with PYthon or WARRIOR ear tags begin to exhibit a significantly increasing incidence of horn fly infestation. By the end of the study, PYthon-treated cattle exhibit about 7% control, and WARRIOR-treated cattle exhibit no (0%) control. In contrast, cattle-treated with ear tags according to an embodiment hereof surprisingly still exhibit more than 90% control. The 15-week average levels of control for the three treated groups are: PYthon (78.3%), WARRIOR (70.4%), and Present Embodiment (98.3%)

The foregoing description is considered illustrative only of the principles of the invention. Furthermore, because numerous modifications and changes will readily occur to those skilled in the art, it is not desired to limit the invention to the exact construction and process shown as described above. Accordingly, all suitable modifications and equivalents that may be resorted to that fall within the scope of the invention as defined by the claims that follow.

What is claimed is:

1. A method for controlling arthropod ectoparasite infestation of a domestic animal comprising applying an ear tag to the animal, the tag comprising:
   a pesticidally effective amount of an active ingredient composition that consists of
   a) an avermectin or combination of avermectins as the only active ingredient of the eartag; and
   b) a 1,3-benzodioxole synergist compound or a combination of 1,3-benzodioxole synergist compounds;
   c) the weight ratio of the synergist component (b) to the macrolide component (a) being greater than 1;

impregnated in a polymer resin base from which it can be released, wherein the ectoparasite controlled is at least one of horn flies, *Haematobia irritans irritans*, and buffalo flies, *Haematobia irritans exigua*.

2. The method according to claim 1, wherein the avermectin is abamectin or ivermectin.

3. The method according to claim 1, wherein the avermectin is abamectin.

4. The method according to claim 1, wherein the synergist compound is piperonyl butoxide.

5. The method according to claim 4, wherein the piperonyl butoxide is piperonyl butoxide technical and the weight ratio of piperonyl butoxide technical to avermectin is at least about 2:1.

6. The method according to claim 1, wherein the polymer resin base comprises a polymer selected from the group consisting of polyvinyl chloride, acrylonitrile-butadiene copolymer, polyurethane, chlorinated polyethylene, and mixtures thereof.

7. The method according to claim 1, wherein the resin base comprises, in addition to a polymer, a substance selected from the group consisting of plasticizers, stabilizers, colorants, fluorescents, and mixtures thereof.

8. A method for controlling arthropod ectoparasite infestation in a domestic animal, comprising applying an article to the animal, the article comprising:
   a pesticidally effective amount of an active ingredient composition that consists of
      a) one or more pesticidal compounds of the avermectin-milbemycin class as the only active ingredient of the eartag; and
      b) an aryl aliphatic ether-class synergist compound or a mixture of aryl aliphatic ether-class synergist compounds;
      c) the weight ratio of the synergist component (b) to the macrolide component (a) being greater than 1;
   impregnated in a polymer resin base from which it can be released, wherein the ectoparasite controlled is at least one of horn flies, *Haematobia irritans irritans*, and buffalo flies, *Haematobia irritans exigua*.

9. The method according to claim 8, wherein the article is any one of a tag, collar, band, film, or adhesive strip or patch.

10. The method according to claim 8, wherein the article is an ear tag.

11. The method according to claim 8, wherein the article comprises from about 1% to about 10% by weight of the pesticidal compound(s).

12. The method according to claim 8, wherein the ratio (c) is about 2 or more.

13. The method according to claim 8, wherein the pesticidal compound comprises abamectin or ivermectin.

14. The method according to claim 8, wherein the pesticidal compound comprises abamectin.

15. The method according to claim 8, wherein the aryl aliphatic ether-class synergist compound comprises any of the 1,3-benzodioxole synergist compounds or combinations thereof.

16. The method according to claim 15, wherein the 1,3-benzodioxole synergist compound comprises piperonyl butoxide.

17. A method according to claim 1, wherein the animal is domestic cattle.

18. A method for controlling arthropod ectoparasite infestation of a domestic animal comprising applying an ear tag to the animal, the tag comprising:
   a pesticidally effective amount of an active ingredient composition that comprises
      a) a macrolide component comprising an avermectin; and
      b) a synergist component comprising a 1,3-benzodioxole synergist compound;
      c) the weight ratio of the synergist component (b) to the macrolide component (a) being greater than 1;
   impregnated in a polymer resin base from which it can be released, wherein the ectoparasite controlled is at least one of horn flies, *Haematobia irritans irritans*, and buffalo flies, *Haematobia irritans exigua*, and wherein the method achieves at least 80% control of either horn flies or buffalo flies for a 15 week period.

19. A method according to claim 18, wherein the macrolide component is abamectin and the synergist component comprises piperonyl butoxide.

20. A method according to claim 18, wherein the macrolide component comprises 8% by weight abamectin and 20% by weight piperonyl butoxide.

21. A method according to claim 18, wherein the animal is domestic cattle.

22. A method according to claim 18, wherein the method achieves at least a 90% control of either horn flies or buffalo flies for a 15 week period.

* * * * *